United States Patent [19]
Fujiwara et al.

[11] Patent Number: 6,007,831
[45] Date of Patent: Dec. 28, 1999

[54] SOAP BARS HAVING QUICK KILL CAPACITY AND METHODS OF ENHANCING SUCH CAPACITY

[75] Inventors: Mitsuko Fujiwara, Urbana, Ill.; Carol Vincent, Wanaque, N.J.; Kavssery Ananthapadmanabhan, Highland Mills; Michael Paul Aronson, West Nyack, both of N.Y.

[73] Assignee: Lever Brothers Company, New York, N.Y.

[21] Appl. No.: 09/004,356

[22] Filed: Jan. 8, 1998

[51] Int. Cl.$^6$ .......................... A01N 25/00; C11D 13/00; A61K 7/00; A61K 31/20
[52] U.S. Cl. ....................... 424/405; 252/367.1; 424/401; 510/137; 510/141; 510/447; 514/558; 514/975
[58] Field of Search ..................................... 424/401, 405; 514/558, 975; 510/447, 141, 137; 252/367.1

[56] References Cited

U.S. PATENT DOCUMENTS

| | | |
|---|---|---|
| 3,043,778 | 7/1962 | Kelly et al. . |
| 4,704,223 | 11/1987 | Gupta et al. . |
| 4,714,563 | 12/1987 | Kajs et al. . |

FOREIGN PATENT DOCUMENTS

| | | |
|---|---|---|
| 0014502 | 8/1980 | European Pat. Off. . |
| 0537964 | 4/1993 | European Pat. Off. . |
| 2243615 | 11/1991 | United Kingdom . |
| 2317396 | 3/1998 | United Kingdom . |
| 97/47722 | 12/1997 | WIPO . |

OTHER PUBLICATIONS

International Search Report Application No. PCT/EP 98/08541 mailed Jun. 14, 1999.

*Primary Examiner*—Shelley A. Dodson
*Assistant Examiner*—Marina Lamm
*Attorney, Agent, or Firm*—Ronald A. Koatz

[57] ABSTRACT

The present invention relates to soap bar compositions in which, by carefully selecting components that are highly surface active, yet soluble enough to deliver antibacterial effect, applicants are able to provide enhance quick-kill (i.e., 60 seconds or less).

5 Claims, 5 Drawing Sheets

SOAP BARS HAVING QUICK KILL CAPACITY AND METHODS OF ENHANCING SUCH CAPACITY

FIELD OF THE INVENTION

The present invention relates to bar compositions (primarily pure soap bar compositions or compositions in which soap is greater than 60%, preferably greater than 80% of surfactant composition). In particular, the invention relates to bar compositions, preferably comprising a bactericide, having the capacity to quickly kill (i.e., 60 seconds or less, preferably 30 seconds or less) enhanced amounts of bacteria. Specifically, by incorporating higher levels of high surface active, adequately soluble soaps (e.g., high nut oil soaps) and/or counterions which are relatively more water soluble (e.g., K or NH4 rather than Na), bacterial quick kill is enhanced. While not wishing to be bound by theory, adequate solubility of high surface active soaps and counterions which enhance solubility of soaps are believed to allow soaps to more quickly interact with bacteria.

The invention is further concerned with a method of ensuring soaps are more soluble/surface active (thereby enabling anti-bacterial activity) by manipulating the levels of "more" soluble soap in a soap comprising a mixture of more "more" soluble to "less" soluble soap such that zein dissolution ratio is greater than 1 (i.e., relative to tallow (82) -coco (18) sodium soap); or by using more soluble counterions (e.g., K rather than Na).

As noted, one measure of how much soap of maximum surface activity is in effect being "delivered" for anti-bacterial effect (how soluble the soap is) is how well the composition solubilizes zein. Thus, the invention is further concerned with providing the greatest deliverable amount of compounds of maximum surface activity and having zein dissolution above a defined level (zein dissolution ratio greater than 1).

BACKGROUND

Germicides or antibacterial agents used to provide anti-bacterial efficacy to skin cleansing compositions are known in the art. Thus, for example, bars containing bacteriostats such as Triclosan (DP300) or Triclocarbon (TCC) are known.

Bacteriostats inhibit the growth of bacteria on skin when they are deposited on the skin. Thus, everything else being equal, the extent of antibacterial activity in any soap bar has until now (measured by long-term substantive effort) been dependent on the nature and amount of antibacterial in the soap bar.

The efficacy of anti-bacterial activity of skin cleansing products containing bacteriostats, however, can be measured in a variety of ways.

The efficacy of anti-bacterial activity of skin cleansing products containing bacteriostat, for example, are generally measured in two types of assays. The first type measures the effect of anti-bacterial agents deposited on skin and is thus reflective of substantively effects. The second type measures the ability of the formulation to cause quick kill (less than 1 minute) of bacteria as determine by in-vitro solution tests.

The time of contact of bacteria with the cleanser in the in-vitro, short time kill assay is somewhat reflective of cursory wash conditions. In fact, cursory wash may take much less than one minute.

Since many or most people who wash with soap bars may not use the bar for longer than a few seconds (average wash time for children may be 10 seconds or less), it becomes apparent that there is a need to deliver anti-bacterial activity in a short period of time (e.g., 60 seconds or less, preferably 30 seconds or less) and, therefore, ways for reassuring quick-kill effect on bacteria are quite critical.

In this regard, the applicants have unexpectedly discovered that immediate bactericidal activity, i.e., quick kill of bacteria, is a function not of the anti-bacterial agent, but rather of the soap, specifically its molecular solubility and surface activity. Thus, factors which enhance both molecular solubility and surface activity increase the anti-bacterial activity under quick kill conditions. Moreover, applicants have found that higher molecular solubility and surface activity correlates with higher zein dissolution by the soap (zein is a relatively insoluble corn protein and the ability of the soap/surfactant to solubilize zein reflects its ability to interact with proteins). That is, higher zein dissolution is essentially a reflection of the ability of the soap to interact with bacterial membrane proteins and cause its kill.

It is well known that soap bars are made with both soluble (e.g., coco soaps), and insoluble (e.g., tallow soap) components. When the soluble fraction dissolves, it can exist in the form of monomeric species in the low concentration range and form aggregates called micelles at some critical concentration defined as CMC. Thus, CMC for a pure component represents the maximum level of its monomeric species available in the aqueous phase. The aqueous solubility and the CMC of soaps and other surfactants decrease with increase in hydrocarbon chain length. The surface activity of the surfactant, on the other hand, increases with increase in chain length. Thus, solubility and surface activity show opposite trends with increase in chain length (e.g., less soluble and more surface active). For a soap molecule to interact with bacteria and cause its kill, it has to be present in the aqueous phase and bind to the membrane when exposed to bacteria. It is generally believed that monomers bind to membranes and the micelles essentially act as a reservoir of monomers. The extent of binding increases with increase in the surface activity of the molecule, provided it is available in the aqueous phase. Thus, for increasing the quick kill, at a given temperature, there should be sufficient amount of highly surface active soap molecules in a monomeric form available for interaction with the bacteria. This implies that the soap molecules should have high surface activity, high CMC and adequate solubility. For this reason at a given temperature there exists an optimum chain length which exhibits adequate solubility and surface activity to bind to the bacteria. At room temperature this optimum chain length for soaps is about C12.

For a given chain length soap, its molecular solubility can also be increased by appropriate choice of counterions. For example, it is known that the solubility of the soaps follow the order: NH4 soaps or triethanolamine soaps>K soaps>Na soaps. Thus, the antibacterial activity of soaps also can be expected to follow the order: NH4 soaps>K soaps>Na soaps. Therefore, for a given soap system, its immediate kill activity can be enhanced simply by changing the counterions from Na to K or NH4. As noted previously, another method of increasing the solubility is by simply increasing the "soluble" fraction (for a given temperature) of the soap in the bar.

The net effect of solubility and surface activity is reflected in bacterial kill as well as in zein solubilization.

BRIEF SUMMARY OF THE INVENTION

In one embodiment, the present invention relates to soap bar compositions (i.e., greater than 60% soap), optionally comprising antibacterial compounds which compositions are able to deliver "quick kill" antibacterial effect. Specifically, by utilizing all or a fragment of soap component having optimal solubility and surface activity, the bars provide enhanced quick kill (e.g., ability to kill in about 60 seconds or less) effect. For example, the compositions provide enhanced quick kill effect relative to a standard tallow -coco-Na soap bars.

More specifically, by first selecting the most surface active, yet still soluble (e.g., chain length sufficiently long to be surface active but not so long that it won't dissolve) soap compound (or fraction of soap) and then manipulating this soap (by either increasing percentage of said compound or fragment relative to all soap and/or by using certain counterions), the quick kill effect is seen. The fraction of surface active, yet still soluble soap should be such that zein dissolution ratio is higher than 1: Generally the lower the ratio of tallow to cocoate, the higher this zein dissolution ratio will be. Thus, less tallow and more cocoate is generally desirable.

In a second embodiment of the invention, the invention provides a method to ensure that the greatest surface activity soap (comprising part or all of the soap component) is solubilized. This effect, in turn, is achieved by manipulation of counterions (some counterions make a given chain length soap more soluble than others) and/or manipulation of soap fragments in the soap composition (e.g., establishing ratio of less "soluble", higher chain length soap to more "soluble" lower chain length soap such that zein dissolution ratio is greater than 1).

DETAILED DESCRIPTION OF THE INVENTION

The present invention relates to composition comprising 60% to 98% fatty acid soap. By fatty acid soap is meant a $C_8$ to $C_{22}$ saturated or unsaturated, substituted or unsubstituted carboxylic acid soap. By first selecting a soap component comprising the most surface active, yet still soluble soap and then manipulating the selected soap (by increasing the concentration of the selected soap relative to other fatty acid soaps; the "selected" soap fraction may comprise 100% of all fatty acid soap present) and/or by selecting a counterion to ensure the most surface active soap can be solubilized, it is possible to provide bars with quick kill capacity.

One indicia of surface activity is low surface tension (low surface tension correlates with high surface activity which in turn correlates with good antibacterial activity) and one indicia of solubility is higher CMC (higher CMC correlates with tendency to be more water soluble). Thus, there is an attempt to find the balance of maximum surface activity while maintaining solubility by finding soaps which have adequately low surface tension (i.e., surface active enough to provide quick kill antibacterial effect), yet high enough critical micelle concentration/solubility. Applicants have found this balance is met when soap fractions are selected such that ratio of more "soluble" fraction (e.g., cocoate) and less "soluble" fraction (e.g., tallowate) gives zein dissolution ratio of greater than 1. For example, when ratio of tallowate to cocoate is 82/18, zein dissolution ratio is 1. When, however, tallowate level is lowered, zein dissolution ratio is above 1 and this correlates with enhanced bactericidal activity (see FIG. 3).

The invention is described in greater detail below.

Soap

The present invention relates to bar compositions comprising of 50% fatty acid soap, preferably 60 to 98%, more preferably 70% to 95% of the soap bar composition.

In general soaps are defined as the alkali metal salts of natural or synthetic aliphatic (alkanoic or alkenoic) acids having about 8 to 24, preferably 12 to 20 carbon atoms.

In the context of the present invention, selection of soap chain lengths (or mixture in which one or two chain lengths predominate over other chain length) is critical. While not wishing to be bound by theory, this is believed to be because the chain length is to be directly correlated to both surface activity and solubility. Thus, for example, while a $C_{14}$ chain length is very surface active (has not so high surface tension), it is not particularly soluble (has low CMC). Conversely, while a $C_8$ soap is soluble (high CMC), it is not very surface active (surface tension too high). The perfect balance between surface activity and solubility (at room temperature) is struck by a $C_{12}$ soap. It should be understood that the balance may shift at higher temperature where higher chain length soap, for example, may be more soluble.

Another way of controlling solubility is through level of unsaturation. Thus a mono-unsaturated or di-unsaturated $C_{18}$ for example, will be surface active and yet still solubilize.

In the bars of the invention, once the most surface active soap which is still adequately soluble is found, this can be used to establish quick kill capacity (ability to kill 99.9% bacteria in 60 seconds or less, preferably 30 seconds or less) in the final bar composition.

Specifically, by manipulating the concentration of "selected" soap (can be a minimum fraction or all of the soap component), quick kill capacity can be established.

In addition, the counterions on these soaps can be manipulated to show quick kill capacity even more. Thus, for example, triethanolamine is better than potassium which is superior to sodium. Counterion manipulation seems to work only with soaps which are selected by chain length criteria because apparently other soaps, even if you increase their solubility a little by using counterions, are not sufficiently soluble and counterions would have little or no effect.

Other Surfactants

Although selection of soap to control balance between solubility and surface tension is primarily intended for predominately or exclusively soap bars (i.e., comprising 50%–98% by wt., preferably 60–98%, more preferably 75–98% by wt. of composition), the bars may also comprise small amounts (0%–40%, preferably 1% to 25% by wt.) of other surfactants selected from anionic, nonionic, zwitterionic and cationic surfactants.

Halogenated Bactericide

The bacteriostats which are preferably used in the liquid cleanser compositions of the are generally halogenated bacteriostats. The first bacteriostats (chemicals which control bacteria which in turn cause sweat to break down into malodorous components) were introduced into soap bars about 1950.

The most widely used of these are hexachlorophene; chlorohexidine; 3,4,4'-trichlorocarbanilide; 3,4',5-tri-bromosalicylanilide; 4,4'-dichloro-3'-(trifluoromethyl) carbanilide; and 2,4,4'-trichloro-2'-hydroxy diphenyl ether.

The bacteriostat is used on the compositions of the invention in an amount ranging from 0.0% to 10% by weight, preferably 0.01 to 8% by weight, more preferably 0.05 to 5% by weight of the composition.

Method of Providing Quick Kill

In a second embodiment of the invention, the invention relates to a method of enhancing quick kill (killing at least 99.9% bacteria in 60 seconds or less, preferably 30 seconds or less) by using soap bar compositions having 75% to 98% by wt. fatty acid soap, 0.0 to 10% by wt. halogenated bactericide, 0 to 20% by wt. non-soap surfactant, wherein said method comprises first selecting a fragment (or all) of soap component (a) to obtain most surface active (low surface tension), yet soluble (high CMC) soap measured at given condition (e.g., room temperature), and manipulating either concentration of selected soap so that ratio of "soluble" to less "soluble" soap yields, zein dissolution ratio greater than 1 and/or by manipulating counterions (using more "soluble" counterion).

EXAMPLES

The following composition was used to show effect on bacteriostat activity.

| Lifebuoy | |
|---|---|
| Na soap | 85.7%* |
| Triclosan | 0.25% |
| TCC | 0.01% |
| Glycerol | 1.0% |
| H$_2$O | 11.1% |
| NaCl | 1.0% |

*ratio of tallowate to cocoate is 82/18
TCC = Triclocarbon

Protocol
Bactericidal Contact Time Assay
(Curry, J.C., Soap & Chemical Specialties, March, 1968; A Modified Version of the "Curry" Test was Used to Stimulate Hand Washing Conditions)

All soap bar solutions were prepared in sterile deionized water and evaluated at concentrations of 0.5%, 1%, 2%, 4% and 8% w/w. The solutions were constantly stirred in a water bath at 30° C.

The activity of the soap bar solutions was evaluated against three strains of Gram positive bacteria (*Staphylococcus aureus* ATCC #6538, *Staphylococcus epidermidis* ATCC #155, and *Staphylococcus epidermidis* ATCC #12228) and two strains of Gram-negative organisms (*Klebsiella pneumoniae* ATCC # 4352 and *Escherichia coli* ATCC #10536). *S. epidermidis* and *S. aureus* are common skin resident bacteria, and the other bacteria are representative of those found primarily as transients on the skin. Two consecutive broth transfers of each bacterial culture were made using Difco Nutrient Broth. All cultures were incubated for 24 hours at 34° C. The second day broth cultures (~$10^{18}$ cells/ml) were used in the test and diluted in 0.1% peptone water to ~$10^6$ cells/ml.

Five ml of Microbial Content Test Agar (Difco) containing 0.5% Tween 80 and 0.07% lecithin as neutralizers to inhibit further action of germicides and 1% dextrose (LMCTA) was dispensed into specially-designed oval tubes. One ml of each product solution was pipetted into 25×100 mm medication tubes in a rack held at room temperature. One ml of the culture inoculum containing ~$10^6$ cells/ml was added to the test solution and timing started using a stopwatch. The mixtures were sampled at 10, 20 and 30 seconds. The samples were withdrawn using a 0.01 ml calibrated loop and immediately placed into oval tubes containing the molten agar. The agar containing the sample was gently mixed and the tube slanted in a rack to allow hardening. This process was repeated for each product/organism combination. The racks of tubes were inverted and incubated at 34° C. for 24 hours. The number of colonies in each tube was enumerated using a Quebec Colony Counter and an oval tube adapter.

Culture control counts were made to determine the initial density of the organisms. Each $10^6$ cells/ml culture preparation was diluted thousand fold by preparing three 1:10 serial dilution's in 9 ml peptone water. In a control medication tube, 1 ml of this dilution was added to 1 ml of sterile 0.1% peptone water (instead of product). Eight replicate samples were withdrawn with a 0.01 ml calibrated loop, placed into the agar tubes and incubated as above. The colony counts were converted to log (CFU/ml) to demonstrate the actual number of cells remaining in solution after contact with the soaps.

CMC

CMC=Critical Micellar Concentration is simply a standard measurement of concentration at which soap/surfactant monomers aggregate to form micelles. Higher CMC is generally associated with greater monomer solubility (i.e., monomers tend to stay in solution before forming micelles).

Zein Testing 1.5% of zein was stirred in 30 ml of 1% surfactant solution at room temperature for 1 hour. The mixture was centrifuged at 2000 rpm for 30 minutes.

The zein pellet was soaked in 10 ml of water for 30 min and dried under vacuum in 45° C. oven for 48–72 hours until all water evaporated. The % difference in the weight of zein was taken as the zein solubility of the surfactant.

Generally, according to the invention, enhanced zein is associated with increased solubility (e.g., more soluble soap is free to interact with protein and enhance zein scores).

Example 1

The present invention provides that by selecting compounds which are surface active, yet soluble, it is possible to deliver strong antibacterial activity quickly (i.e., greater than 99.9% kill in 60 seconds or less). One indicia of surface activity is low surface tension (low surface tension correlates with high surface activity which in turn correlates with good antibacterial potential), while one indicia of solubility is critical micelle concentration (if it takes compound higher concentration to form micelle, i.e., higher CMC, this generally indicates the monomeric compound is more water soluble).

In addition, zein solubility above certain level (e.g. zein solubility ratio above 1, e.g., measured by tallowate to cocoate ratio of 82/18 being equally to 1) means that the surfactant solubilizes protein and therefore may have higher tendency to solubilize bacteria. More specifically, the zein dissolution ratio is the ratio of the percent of zein dissolved by a particular composition divided by the percent of zein dissolved by an 82/18 tallow to cocoate sodium soap when compared at same weight percent of the composition to the soaps. Zein solubility (Zein dissolution ratio) thus is indicia of whether a compound is surface active and can be delivered (i.e., is active against bacteria). Generally, higher zein correlates to greater deliverability.

Taking these factors into account, applicants obtained measurements for the critical micellar concentration (CMC) and surface tension at CMC at 25° C. for various sodium soaps (Data taken from A. N. Campbell and G. R. Lakshminaraganam, Can. J. Chem. (1965), 43, 1729–1737) as follows:

|  | CMC* | Surf. Tension** |
| --- | --- | --- |
| C8 | 0.35 M | 39 dyn/cm |
| C10 | 0.095 M | 37 dyn/cm |
| C12 | 0.023 M | 23 dyn/cm |
| C14 | 0.007 M | 34 dyn/cm |

*higher correlates with greater solubility
**lower correlates with greater surface activity From this data, it can be seen that $C_8$, $C_{10}$ and $C_{12}$ (high CMC) tend to solubilize better than $C_{14}$. Thus, although $C_{14}$ is as surface active as $C_{10}$ or $C_{12}$ (surface tensions are comparable), $C_8$ and $C_{10}$ would be more deliverable. The best candidate, however, is $C_{12}$ since this has the best surface activity (lowest surface tension) and a CMC high enough to insure it will be solubilized/delivered.

Moreover, this is confirmed from an analysis of zein data shown below.

|  |  | Bacterial Kill ($\Delta$Log (FU/ml)) | |
| --- | --- | --- | --- |
|  | Zein | 0.5% Soap/Surfactant | 1.9% Soap/Surfactant |
| C8 Soap | 4% | 0 | 0 |
| C10 Soap | 17% | 0 | 3.2 |
| C12 Soap | 77% | 2.4 | 3 |
| C18:1 Soap | 67% | 2.1 | 2.5 |
| C18:2 Soap | 67% | 2.7 | 3.0 |
| Lifebuoy bar (82/18 sodium soap) | 69% | 0 | 2.1 |
| Sodium Dodecyl Sulfate | 90% | 3 | 3.4 |

The zein data show that surface activity of $C_8$ and $C_{10}$ soaps are nowhere close to that of $C_{12}$, specifically at lower concentrations. That is, high zein score confirms that $C_{12}$ is being solubilized and has good surface activity against zein. This would be expected to be exactly the same against bacteria rather than zein, i.e., $C_{12}$ has the best combination of surface activity and solubility (as confirmed by the high zein score). Sodium dodecyl sulfate, being significantly more soluble than $C_{12}$ soap, shows even higher zein dissolution than the $C_{12}$ soaps. This is also reflected in the higher antibacterial activity of sodium dodecyl sulfate. High zein scores for C18:1 and C18:2 (mono and di-unsaturated carboxylic acids) also show these components have good combination of surface activity and solubility.

Example 2

Soap chain lengths were further tested as follows:

The bactericidal activity of sodium soaps again *S. aureus* was dependent on its chain length and the degree of unsaturation. The bactericidal activity increased with increasing soap concentration and increasing contact time with the bacteria. Bacteriocidal activity ($\Delta$ log CFU/ml) above 3 represents over 99.9% kill of bacteria. The general order of bactericidal activity given below shows that sodium soaps which have shorter or unsaturated chains exhibited activity while soaps with long, saturated hydrocarbon chains (C14, C16, and C18) did not exhibit any activity:

$C12 \sim C10 > C18:2 > C18:1 > C8 > C14 \sim C16 \sim C18$

The trend showing lower chain lengths and unsaturates are generally superior to longer chain lengths (e.g., $C_{16}$ & $C_{18}$) is definitely observed.

Again, while not wishing to be bound by theory, this is believed to occur because $C_{12}$ is the longest chain length soap (most surface active) which also solubilizes and therefore is free to attack either zein or, more interestingly, bacteria. $C_{14}$ compounds have decent surface activity (similar to $C_{16}$), but simply do not solubilize as well (lower CMC) as $C_{12}$ or $C_{10}$ and, therefore, the effect on bacteria activity is stronger for $C_{10}$ than $C_{14}$.

Example 3

Figure 3:
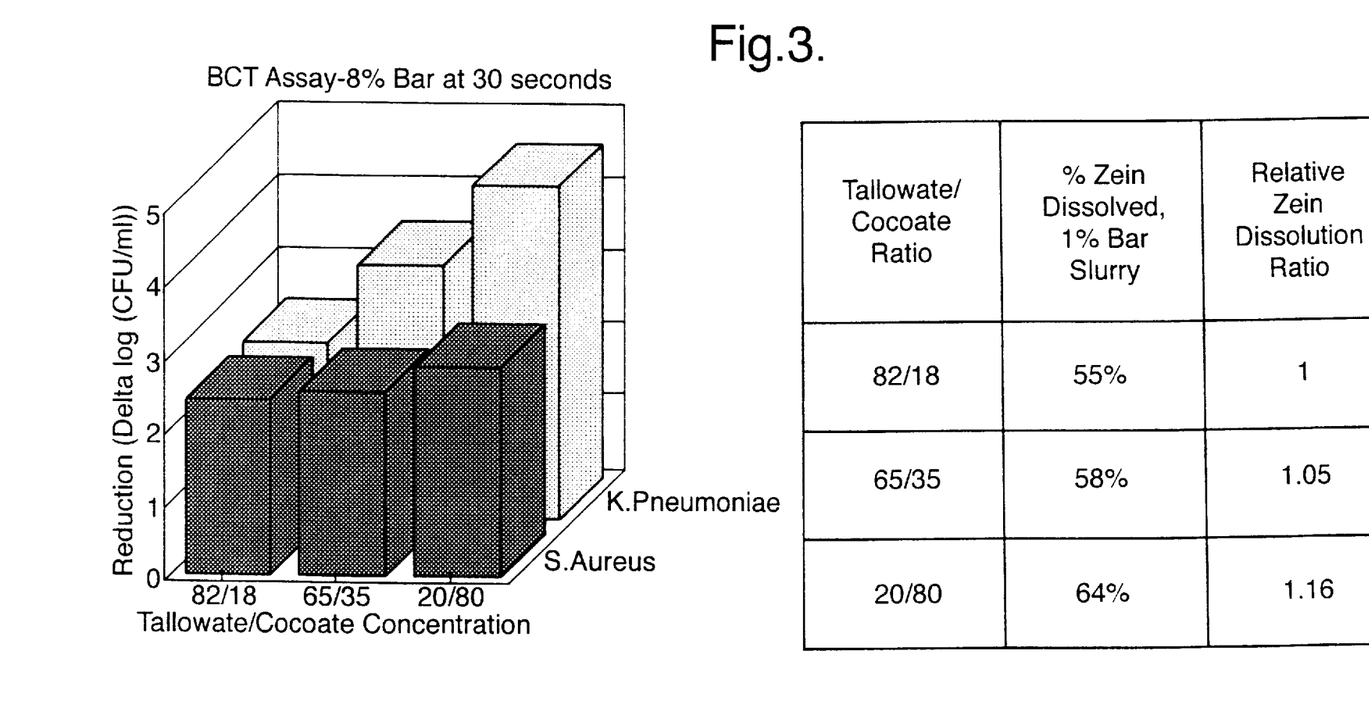
FIG. 3 correlates ratio of less "soluble" longer chain soaps (e.g., tallowate) to relatively more "soluble", shorter chain soap (e.g., cocoate) and effect on bacteria. As seen, when tallowate is decreased, zein dissolution ratio is greater than 1 and bactericidal activity increases.
Figure 4:
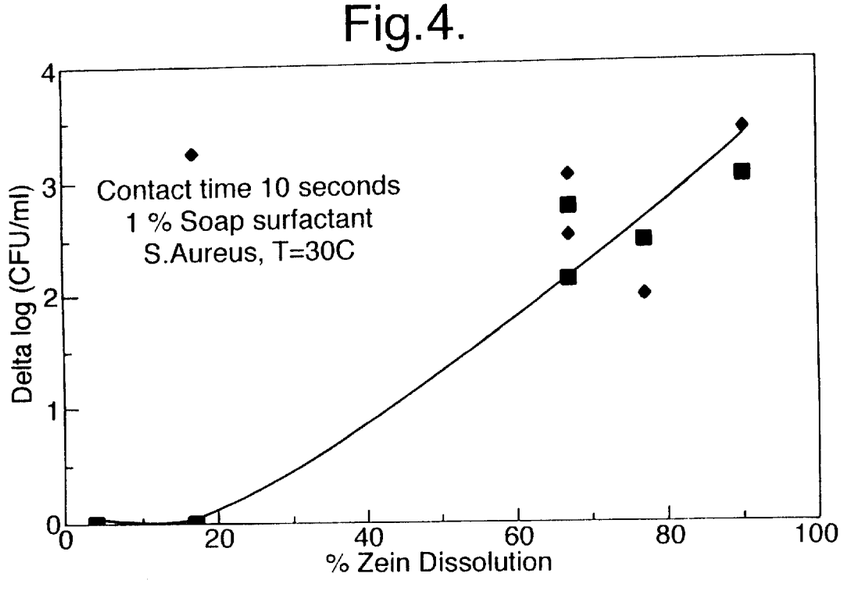
FIG. 4 again shows that, as zein dissolution increases (correlated with lower ratio of tallowate to cocoate or use of more soluble counterions), bactericidal activity increases.
Figure 5:
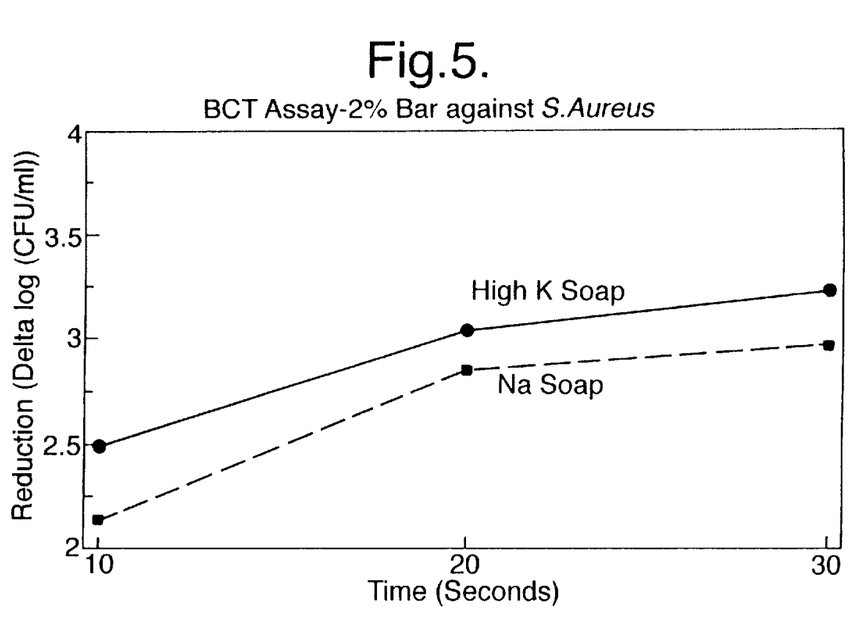
FIG. 5 shows that use of more soluble counterion (potassium versus sodium) increases bactericidal activity.
Figure 6:
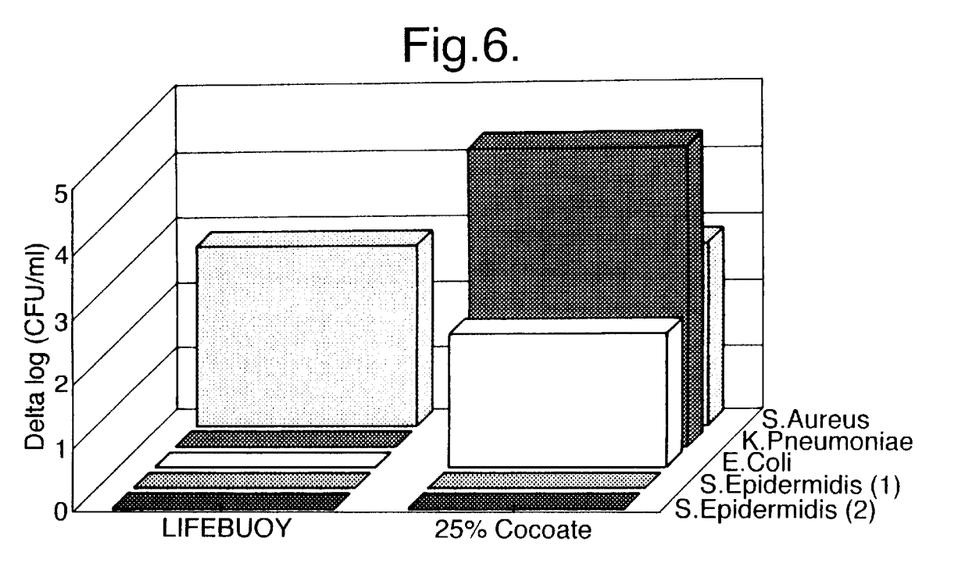
FIG. 6 shows that decreasing ratio of tallowate to cocoate (by adding 25% cocoate to normal 82/18 tallowate/cocoate ratio in Lifebuoy$^{(R)}$) enhances bactericidal activity. Specifically, not only is the composition more effective relative to Lifebuoy$^{(R)}$ against the same bacteria, but it is also effective against bacteria that Lifebuoy$^{(R)}$, normally has no effect against.
Figure 7A:
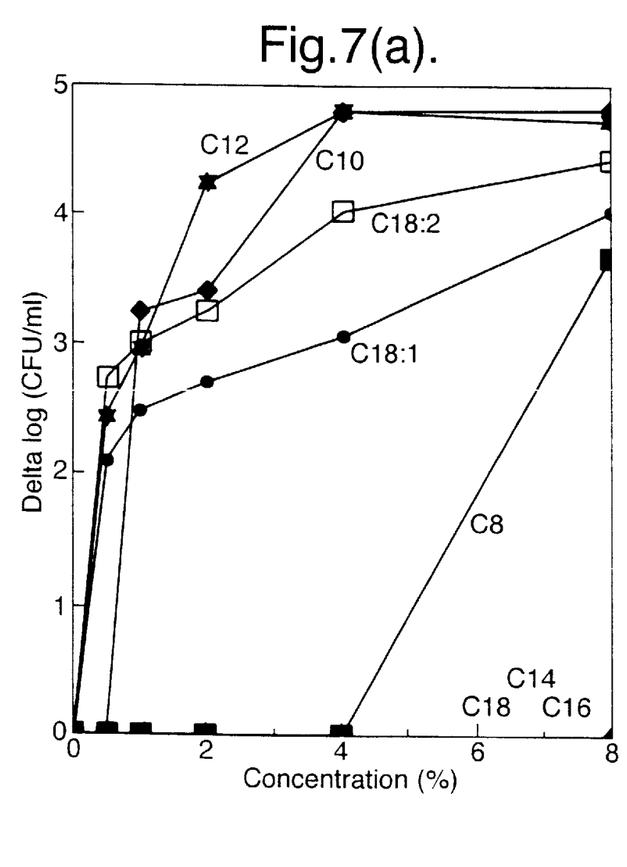
FIG. 7 shows dependence of bactericidal activity on chain length of sodium soap at two different temperatures. For example, at higher temperatures (where $C_{14}$ for example is more soluble), $C_{14}$ exhibits significant bactericidal activity.
Figure 7B:
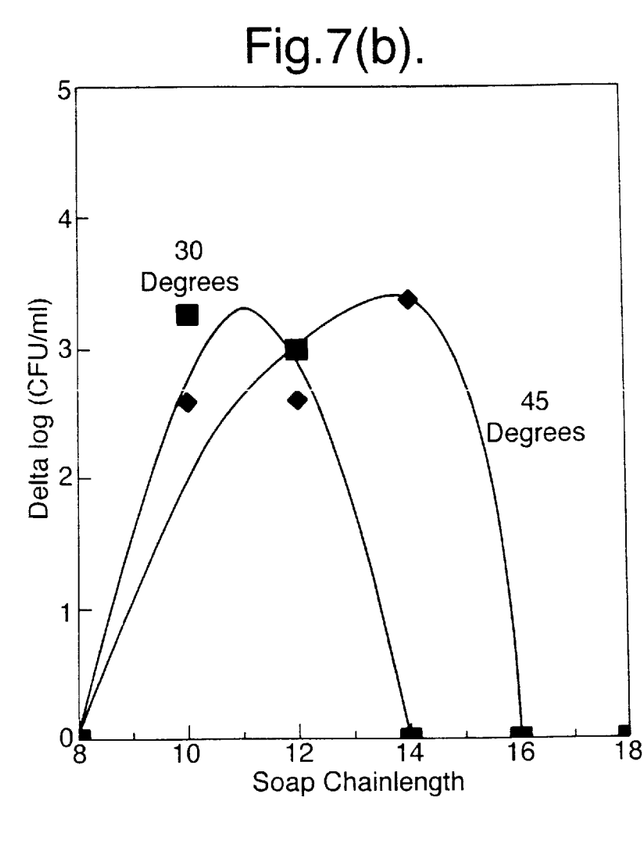

As seen from FIG. 3, processing fraction of more "soluble" cocoate relative to less "soluble" tallowate increased zein ratio (greater than 1) which in turn correlated with increased bactericidal activity.

Effect of Counterion

Figure 1:
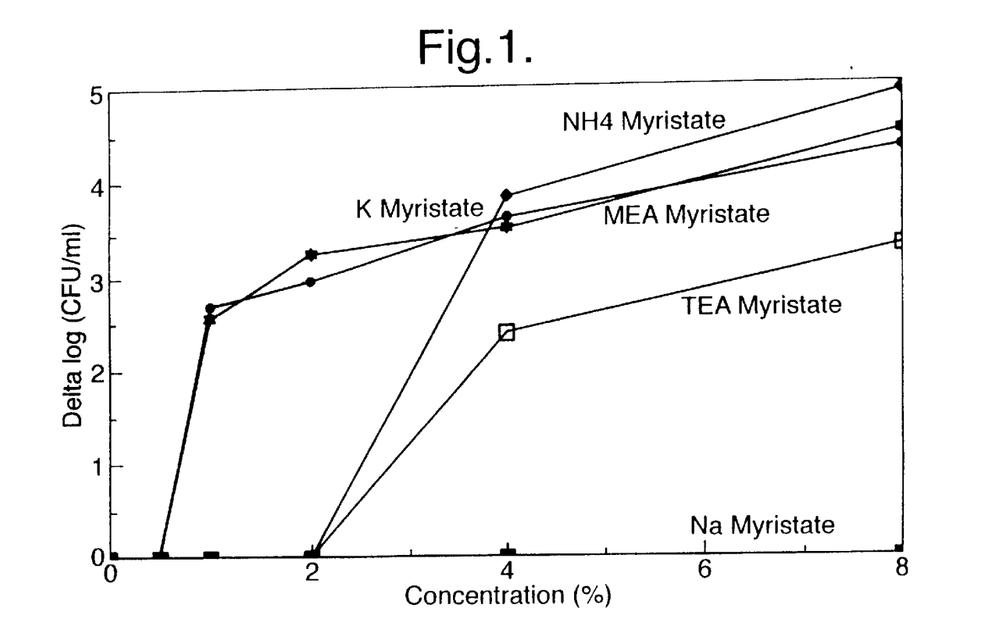
FIG. 1 shows that more soluble counterions such as potassium NH4, MEA or TEA lead to enhancement in bactericidal activity compared to no activity for sodium counterion.

The effect of different counter ions on the bactericidal activity of sodium soaps was investigated. As shown in FIG. 1, changing the counter ion to ammonium, potassium, monoethanolamine (MEA) or triethanolamine (TEA) increased the bactericidal activity of sodium myristate against *S. aureus*. It should be noted that the bactericidal activity of C16 and longer sodium soaps was not improved by changing the counter ion to potassium. While not wishing to be bound by theory, this is probably because the solubility (recall these longer chain lengths generally have lower CMC, correlated with less aqueous solubility) of longer chain soaps was not increased substantially.

Figure 2:
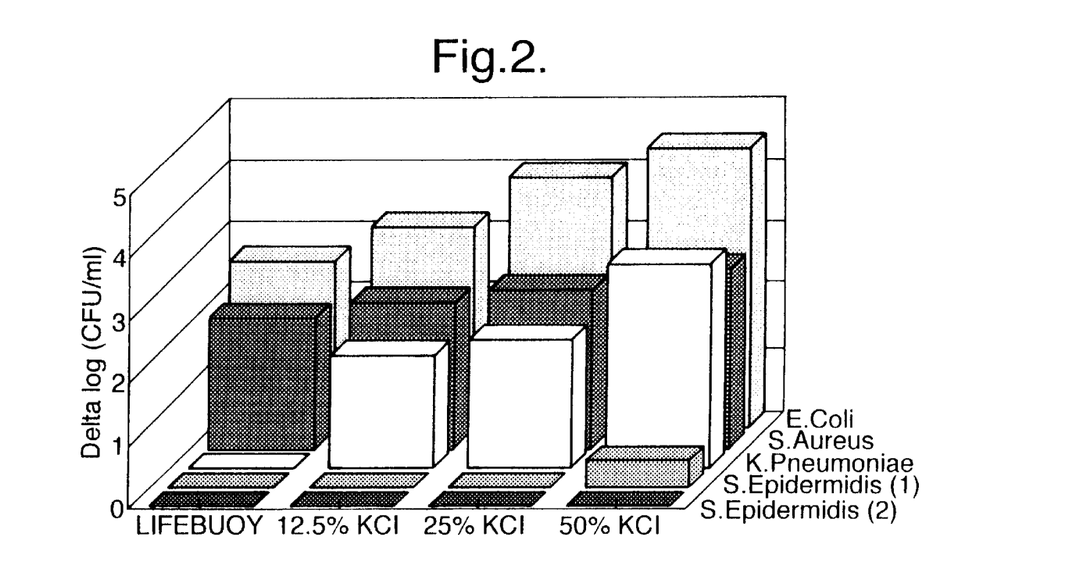
FIG. 2 shows again that using potassium counterion (Lifebuoy$^{(R)}$ composition used sodium) enhances bactericidal activity. As percentage of counterion increases, activity becomes greater. This effect is believed to be due to the fact that potassium makes compound more soluble.

Changing the counter ion to potassium by the addition of KCl to Lifebuoy increased its bactericidal activity. FIG. 2 shows the bactericidal activity of Lifebuoy with varying concentration of KCl against various organisms. Addition of KCl improved the activity of Indonesian Lifebuoy against both Gram-positive and Gram-negative organisms tested except for *S. epidermidis* ATCC 12228.

We claim:

1. A method for enhancing bacterial quick kill in a bar composition such that a bar containing a defined fatty acid soap fraction kills greater than about 99.9% of bacteria in 60 seconds or less, wherein said bar comprises:

(a) 60% to 98% by wt. of a fatty acid soap fraction comprising one or more soaps which are both surface active and sufficiently water soluble to kill bacteria;

(b) 0 to 10% halogenated bacteriostat; and (c) 0 to 20% non-soap surfactant selected from the group consisting of anionic, nonionic, zwitterionic, cationic surfactant and mixtures thereof;

wherein said method comprises selecting at least one soap in said fatty acid soap fraction (a) to obtain the most surface active, still soluble soap component measured under a given condition; and either manipulating the concentration of said soap relative to other soaps in said fraction and/or manipulating the counterion on any soap in said fraction such that zein dissolution ratio is greater than 1;

wherein ratio of 1 corresponds to zein dissolution ratio of bar comprising 82% sodium tallowate and 18% sodium cocoate.

2. A method according to claim 1, wherein the given condition under which soap is measured is room temperature.

3. A method according to claim 1, wherein a counterion on either fatty acid soap or surface active, water soluble soap is triethanolamine.

4. A method according to claim 1, where a counterion either fatty acid soap or surface active, water soluble is potassium.

5. A method according to claim 1, wherein the surface active, water soluble soap comprises greater than 18% of the soap fraction.

* * * * *